United States Patent [19]

Spector

[11] 4,119,097

[45] Oct. 10, 1978

[54] EMERGENCY OXYGEN SUPPLY

[75] Inventor: Donald Spector, Union City, N.J.

[73] Assignee: Applied Research Commodities Industries, Inc., Hyattsville, Md.

[21] Appl. No.: 765,288

[22] Filed: Feb. 3, 1977

[51] Int. Cl.² .............................................. A61M 16/00

[52] U.S. Cl. ...................................... 128/203; 128/202

[58] Field of Search ............... 128/203, 202, 205, 195, 128/191 R, 173 R, 142 R, 146.3, 145 R, 145.7, 145.8

[56] References Cited

U.S. PATENT DOCUMENTS

| | | | |
|---|---|---|---|
| 1,203,391 | 10/1916 | O'Donnell | 128/203 |
| 2,510,712 | 6/1950 | Olowinski | 128/205 X |
| 3,208,449 | 9/1965 | Bartlett, Jr. | 128/203 X |
| 3,530,857 | 9/1970 | Miczka | 128/145.7 X |

*Primary Examiner*—Robert W. Michell
*Assistant Examiner*—Henry J. Recla
*Attorney, Agent, or Firm*—Michael Ebert

[57] ABSTRACT

A portable emergency oxygen supply which may be carried without difficulty by a user and is safe under all conditions. The supply includes a canister containing oxygen-rich gas at relatively low pressure, the canister having a normally-closed valve which is provided with an actuating switch. The valve output is coupled by a feed tube to the interior of an inflatable bellows which is attached to and communicates with a face mask whereby the user is able to repeatedly inhale and exhale the volume of gas enclosed in the bellows, in the course of which he depletes the oxygen contained therein. The oxygen in the bellows is intermittently replenished by operating the switch so that the available oxygen in the canister is fully utilized.

4 Claims, 7 Drawing Figures

EMERGENCY OXYGEN SUPPLY

BACKGROUND OF INVENTION

This invention relates generally to emergency oxygen supplies for human use, and more particularly to a portable oxygen supply having a relatively small and safe reservoir of oxygen, yet making it possible for the user to breathe normally for a period equal to that obtainable from a much larger reservoir.

In terms of mechanical engineering, the human respiratory system consists of an air pump and two liquid pumps. The air pump, which is constituted by the diaphragm and the chest, acts to draw air into the lungs and then force it out again. The two ventricles of the heart function as liquid pumps, the right ventricle pumping its blood into the capillary network of the lungs to bring oxygen-short blood into the proximity of air possessing oxygen. The left ventricle pumps its blood, now rich in oxygen, into the capillary network of the body and thereby conveys rich blood into the tissues in need of oxygen.

Again in terms of mechanical engineering, the lungs may be regarded as a brilliant execution of a poor design, for lungs are inefficient organs, with the exit and entrance for air thereto at one and the same place. There is only a partial interchange of gas with each breathing cycle, and about four-fifths of the air present in the lungs is still there when the next breath begins.

Virtually, no carbon dioxide is present in the normal atmosphere, whereas expired air has about 4% carbon dioxide, and breathing becomes difficult when this percentage in the incoming air rises above 4%. If, therefore, air having the usual 20% of oxygen becomes excessively rich in carbon dioxide, a feeling of faintness is experienced. On the other hand, while oxygen is vital to breathing, one may become unduly stimulated from breathing pure oxygen for an excessive period or suffer lung damage.

Holding the breath is possible for a very limited time, say, about 45 seconds, and thereafter becomes impossible; but should one first take a few puffs of pure oxygen or gasp deeply with ordinary air, the breath can be held for perhaps 2 minutes. All respiratory system factors with respect to the purity of oxygen and the tolerable proportion of carbon dioxide must be taken into account in an emergency air supply to replace or supplement the available air in a given situation.

It is known to provide an emergency oxygen supply in the form of a valve-controlled tank of highly pressurized oxygen whose output is fed to a face mask or inhalator. With a supply of this type, the user wastes most of the available oxygen, and in order to supply sufficient oxygen for a prescribed period, one must provide a pressurized oxygen reservoir requiring a strongly-reinforced tank or canister capable of withstanding high pressures. As a consequence, the tank and the associated high-pressure control are necessarily in heavy-duty form and relatively cumbersome.

Portable air supplies designed for escape from smoke and fume-filled rooms are described in the February, 1975 issue of "Compressed Air Magazine." These supplies involve canisters formed of double-coil steel tubing built to hold pressures in excess of 5000 psig and operating in conjunction with a transparent hood which covers the head of the user to keep toxic fumes out of the eyes and nose. The hood includes an exhalation valve that prevents pressure and $CO_2$ buildup.

Also described in the same article is a Survival Support Device in which an air capsule containing air under 6500 psig provides 8 minutes of breathing air. A safety valve is provided should the pressure buildup to dangerous levels.

An individual suffering from emphysema and in need of an emergency oxygen supply is usually not in good physical condition, and the conventional air or oxygen emergency supply, though portable, nevertheless imposes a taxing burden on this purpose. Moreover, a highly-pressurized tank of oxygen in some situations, as in a fire, is potentially dangerous.

The reason why a conventional oxygen supply is wasteful is that it is designed to feed oxygen to a user in an arrangement which inherently limits its utilization to a single breathing cycle. Though a user in the course of a normal single breathing cycle inhales and exhales a large volume of air, only a small portion of the oxygen contained therein is actually interchanged in the respiratory system, while a far greater portion is taken in and then discharged without any such interchange.

Thus while a normal day's breathing involves about 530 cubic feet of air or a huge volume of air occupying a space of about 8 feet by 8 feet by 8 feet, a person confined within an unventilated chamber having this volume of air would have a sufficient air supply for much more than a day. Or to give an actual example of the ability of an individual to breathe comfortably in a confined space, we shall consider telephone booths in England which are notorious for their tight-fitting doors and lack of effective ventilation. While a telephone booth of this type holds about 37 cubic feet of air, a fair amount of which is displaced by the person making a call, it is still possible for the caller to stay in the booth and breathe with reasonable comfort for at least half an hour.

The reason for this is that the caller, though he is gradually depleting the oxygen in the air and raising the amount of carbon dioxide therein during each breathing cycle in which he takes in a relatively large volume of air, he is doing so only with respect to a small percentage of the oxygen contained in this volume. Consequently, air in the booth may be repeatedly recycled by the respiratory system before it is rendered unacceptable for breathing.

This is not to suggest that no provision be made for ventilating booths or other confined quarters, but only serves to call attention to the remarkable breathing tolerances of the respiratory system, a factor which has not heretofore been exploited in emergency oxygen supplies.

SUMMARY OF INVENTION

In view of the foregoing, it is the main object of this invention to provide a portable and light-weight emergency oxygen supply which may be carried without difficulty by a user and which includes in addition to a supply of oxygen-rich gas, an inflatable breathing bellows, making it possible for a user to rebreathe the same volume of gas and to replenish the oxygen therein only when the gas in the bellows is no longer acceptable.

A significant feature of this invention is that it makes feasible the inclusion in the supply of a relatively small, low-pressure reservoir of oxygen, this reservoir being nevertheless sufficient to supply a user with adequate oxygen for a period equal to that obtainable from a much larger high-pressure reservoir.

Thus with an emergency supply in accordance with the invention, because the oxygen is under relatively low pressure, it may be contained in an ordinary thin-walled aerosol-type spray can having an actuator valve, without any danger of explosion and without imposing a burden on the user, for the oxygen-filled can is light-weight and may be carried without difficulty.

And while the invention lends itself to a light-weight portable arrangement, it does not preclude the use of an oxygen supply in a highly-pressurized tank; for such tanks afford a much larger reservoir of oxygen, and this reservoir, in conjunction with an inflatable bellows permitting re-use of the air and the intermittent replenishment of the oxygen therein, makes it possible to provide breathable air for a much longer operating period than with a conventional pressurized oxygen supply.

Also an object of this invention is to provide an emergency oxygen supply which is provided with an actuating switch to open a valve feeding oxygen into a bellows, which supply may be held and applied to the face by one hand of the user, the hand grasping the canister containing the oxygen also operating the switch whereby the user then has his other hand free for other purposes.

Thus when the emergency supply is carried by a fireman entering a smoke-filled room, the fireman is able to make use of the supply with his left hand while his right hand can be used to carry out firefighting or rescue functions.

Briefly stated, these objects are attained in an emergency supply which includes a canister filled with oxygen-rich gas at relatively low pressure, the canister having a normally-closed valve which when actuated by a switch opens the valve to feed oxygen into an inflatable bellows attached to and communicating with a face mask, such that when the user applies the face mask to his mouth and nose, his breathing is then confined to the air in the bellows.

By intermittently actuating the switch, the depleted oxygen in the bellows may be replenished by the user after several breathing cycles so that the available oxygen in the supply is fully utilized.

OUTLINE OF DRAWINGS

For a better understanding of the invention as well as other objects and further features thereof, reference is made to the following detailed description to be read in conjunction with the accompanying drawings, wherein.

DESCRIPTION OF INVENTION

First Embodiment

Figure 4:
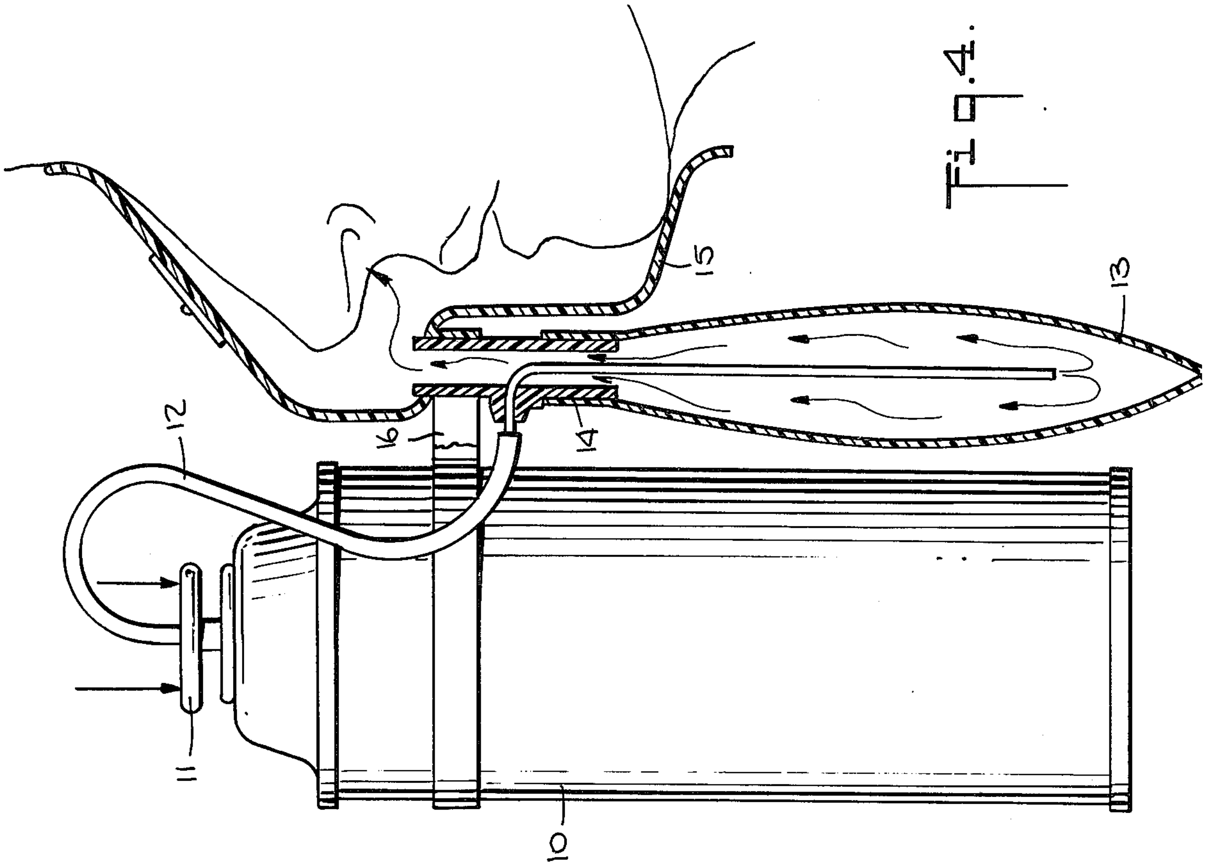
FIG. 4 is a side view of the supply, partly in section.
Figure 1:
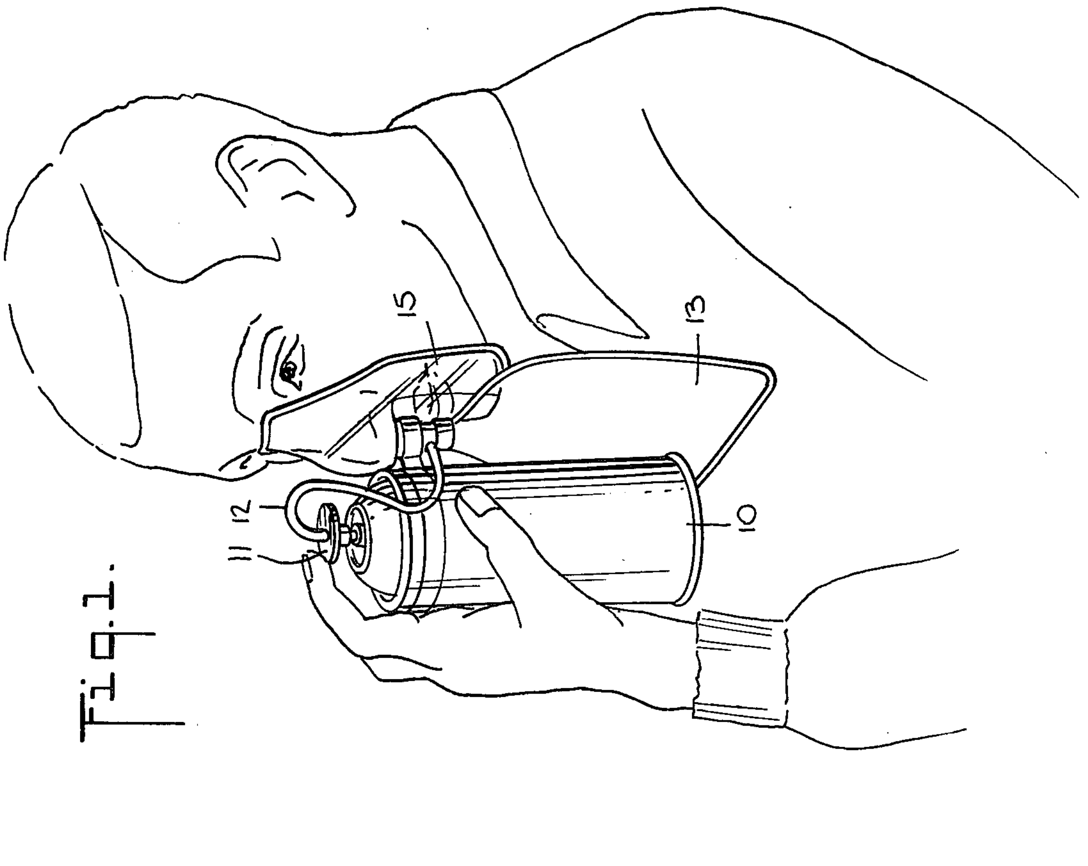
FIG. 1 is a perspective view of one embodiment of an emergency air supply in accordance with the invention.
Figure 3:
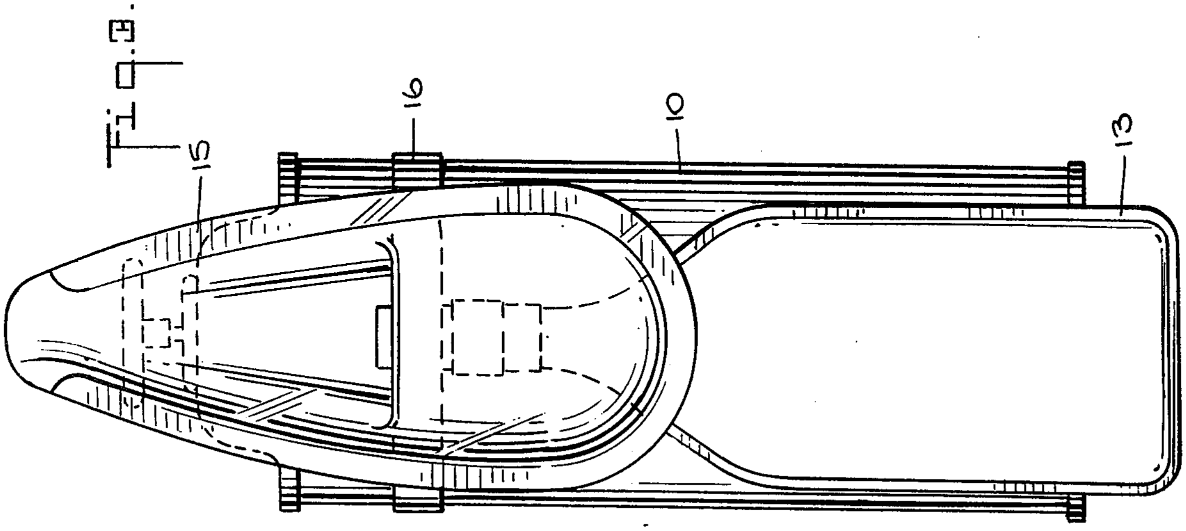
FIG. 3 is a front view of the supply.
Figure 2:
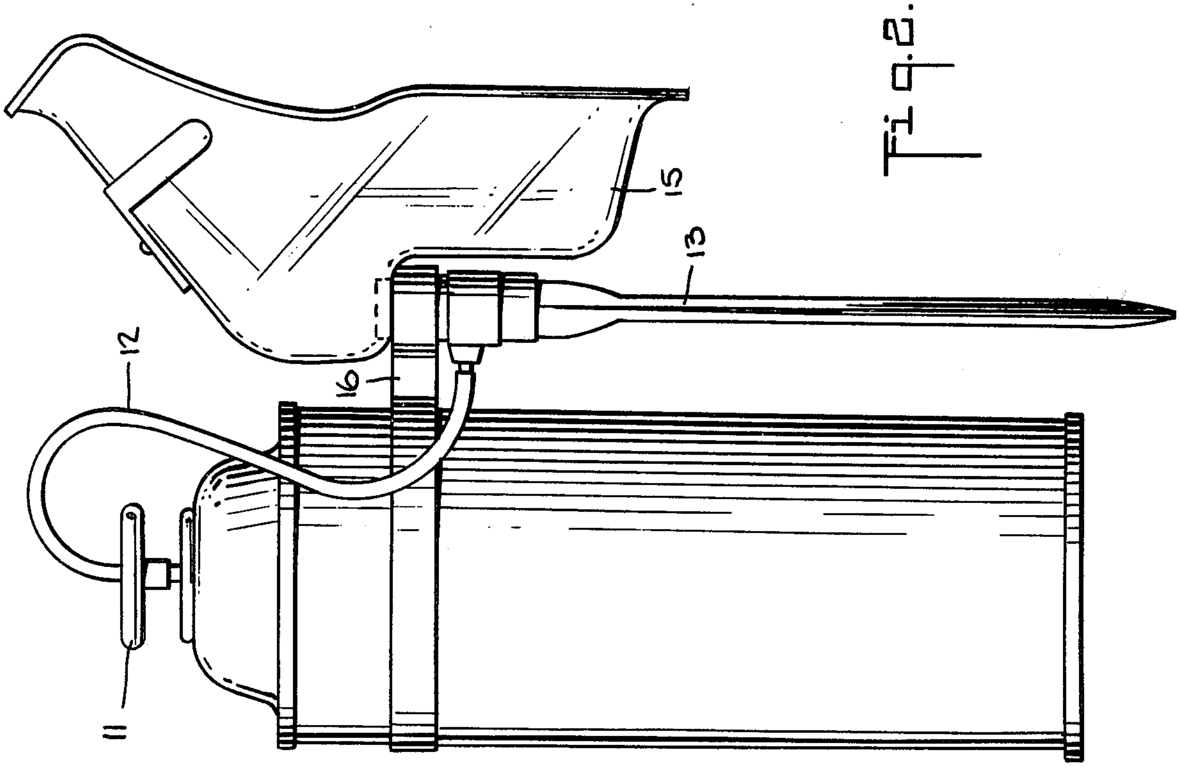
FIG. 2 is a side view of the supply.

Referring now to FIG. 1, there is shown an emergency oxygen supply in accordance with the invention, the supply including a canister 10 which may be a light-weight metal can containing pure oxygen under low pressure, say, 200 psi. In practice, the gas in the canister may be stabilized by a small percentage of carbon dioxide. The appropriate richness of oxygen in the canister is determined by the use for which the supply is intended. Thus in the case of cardiac patients, a reservoir of pure oxygen may not be acceptable because of the unduly stimulating effect of this gas.

Canister 10 is provided with a standard aerosol-type valve (not shown) which is normally closed and is actuated by pressing down on an actuator button 11 on top of the canister. The output of the valve is fed through flexible tube 12 into the interior of a dilatable bellows or sac 13 formed of flexible synthetic plastic material which is non-reactive with oxygen and is heat-resistant.

Bellows 13 is secured to a rigid coupler 14 which is attached to and communicates with the interior of a face mask 15 contoured to fit over the nose and mouth of the user, and to confine breathing to the gas supplied to the mask by the bellows. The face mask is secured to one side of canister 10 by a mounting strap 16 which is clamped into canister 10 and attached to coupler 14.

In use, therefore, as shown in FIG. 1, when the user holds canister 10 in his hand and places his nose and mouth into mask 15, his breathing is confined to the air in bellows 13 which he breathes in and out repeatedly. When the oxygen level in the bellows falls to a level unacceptable for breathing—and this is intuitively sensed by the user when he finds the air difficult to breathe—he refreshes the air with oxygen by actuating switch 11 momentarily and then continues to breathe the refreshed air until another oxygen recharge is necessary. It will be seen that the entire supply can be held in one hand, with a finger thereof used to operate valve switch 11. Hence the other hand is free for other purposes.

At some point in the course of use, when the user senses that the percentage of carbon dioxide in the bellows has risen to an uncomfortable level, he draws the gas from the bellows to deflate the bellows and he breathes out, not into the mask but into the atmosphere, while at the same time feeding a fresh charge of oxygen into the bellows to inflate the bellows with oxygen.

No training period is necessary for the emergency supply; for once the user is instructed in how to use the supply and learns to breathe in and out into the mask to reuse the gas in the bellows, he knows intuitively when the gas is used up and must be refreshed. Just as breathing is a natural process, the user is able to sense when the quality of the air is unacceptable to his respiratory system.

Second Embodiment

Figure 5:
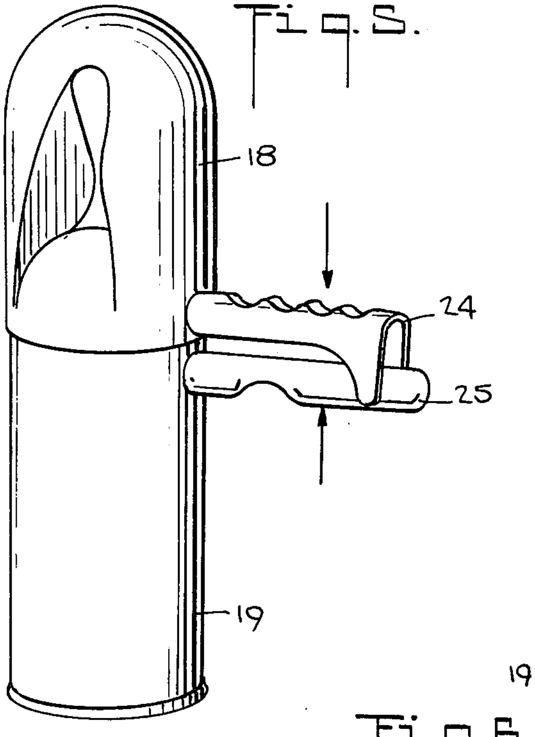
FIG. 5 shows another embodiment of a supply in accordance with the invention.
Figure 6:
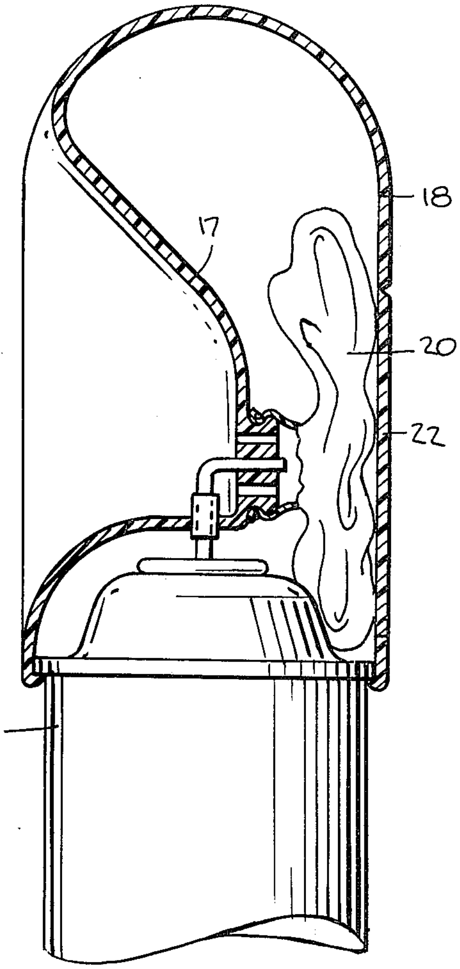
FIG. 6 is a sectional view of the supply with the bellows thereof retracted.
Figure 7:
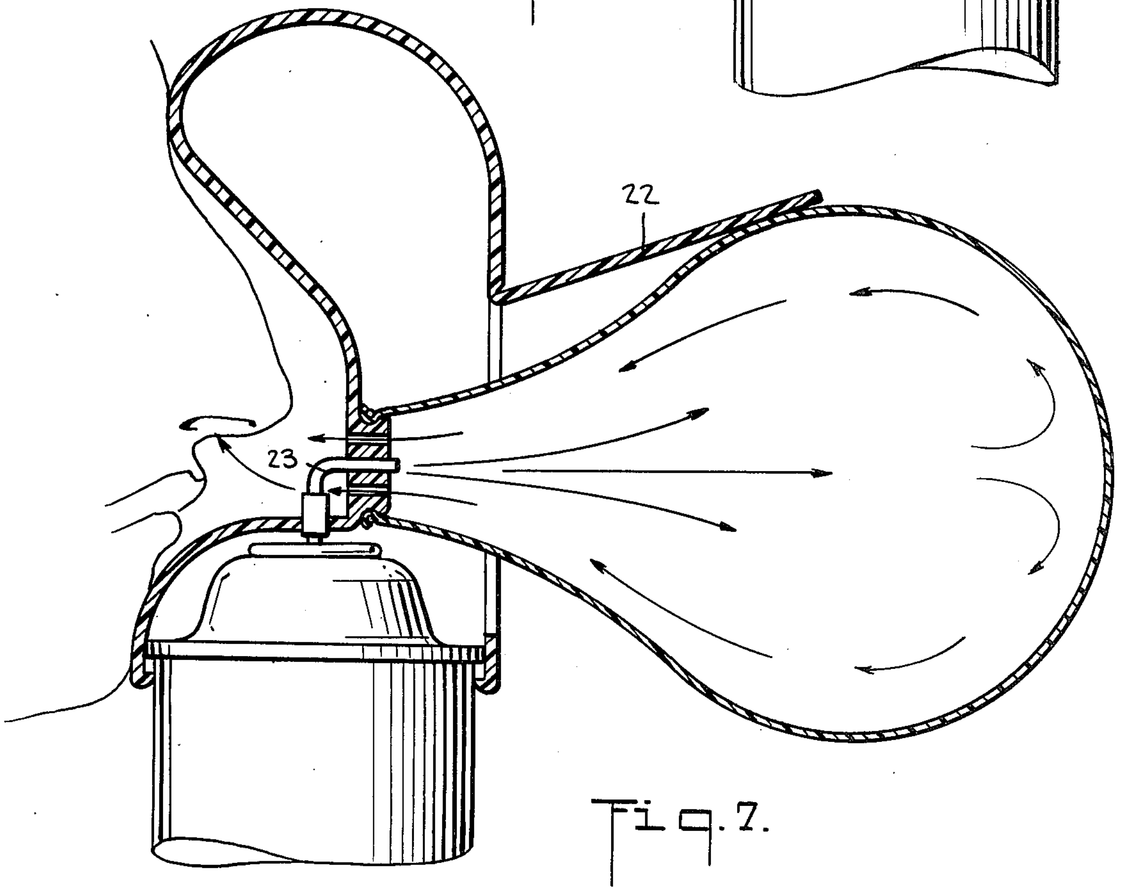
FIG. 7 is a sectional view with the bellows expanded.

In the cylindrical assembly shown in FIGS. 5, 6 and 7, mask 17 is integrated with a transparent dome-shaped cap 18 fitting over a canister 19. Cap 18 is preferably formed of transparent plastic material to minimize interference with vision. When not in use, bellows 20, coupled by an orifice plate 21 to mask 17, is confined within the cap, the cap being provided with a spring-biased trap door 22 which is forced open by the bellows when it is inflated and expands outside of the cap. Cap 20 may be connected to the canister by a threaded coupling ring (not shown), so that the canister when exhausted can be replaced.

Oxygen from the canister valve is fed through a tube 23 into bellows 20, and the actuator for the valve in this instance is in the form of a two-part handle extending laterally from the assembly, the upper handle piece 24 being movable relative to the fixed lower handle piece 25. Thus the assembly may be held by one hand and brought against the face of the user. By pressing the handle, oxygen is supplied to the bellows.

Thus the entire emergency oxygen system is self-contained in a cylindrical assembly formed by the canister and the cap attached thereto. This assembly may be carried by a fireman in a suitably shaped holster strapped to his waist and withdrawn therefrom.

It is important to note that the supply in accordance with the invention is individually rather than automatically regulated in that the user determines for himself when he requires a fresh charge of oxygen rather than depend on a regulator for this purpose which is insensitive to the particular and unique oxygen demands of the user. Also the valve associated with the canister may be of the metered type so that even if a user because of panic or any other reason keeps the valve actuator depressed, only a metered amount of oxygen will be fed to the bellows.

While there have been shown and described preferred embodiments of an emergency oxygen supply in accordance with the invention, it will be appreciated that many changes and modifications may be made therein without, however, departing from the essential spirit thereof. For example, while the oxygen from the canister is fed into the bellows through the orifice plate through which the user breathes the gas in the bellows, the feed into the bellows may be separated from the breathing passage by means of a flexible feed pipe coupled, not to the mouth of the bellows, but to the side wall thereof.

I claim:

1. An emergency oxygen supply comprising:

A. a canister containing oxygen and provided with a normally-closed switch-actuated valve;

B. a mask and bellows sub-assembly constituted by a mask adapted to receive the mouth and nose of a user and to confine breathing to the interior of the mask and an inflatable bellows attached to the mask and communicating therewith;

C. means to feed oxygen from said canister into the bellows and coupled to the output of the valve, whereby when the switch is actuated, oxygen from the canister is fed into and inflates the bellows, to enrich the gas which the user inhales and exhales, and making it possible for the user to breathe the same volume of gas in the bellows until such time as the oxygen therein requires replenishment; and D. a dome-shaped cap fitting over the top of said canister, said mask being integral with a side wall of said cap and forming a part thereof whereby the bellows attached to the mask is normally confined within the interior of the cap, the side wall of the cap opposed to the mask being provided with a spring-biased trap door that, when the bellows is inflated, is forced open by the expanding bellows to permit the bellows to expand outside of said cap.

2. A supply as set forth in claim 1, wherein said cap is formed of transparent material.

3. A supply as set forth in claim 1, wherein said oxygen in the canister is maintained under relatively low pressure.

4. A supply as set forth in claim 1, wherein a relatively small percentage of carbon dioxide is intermixed with said oxygen.

* * * * *